United States Patent
Terakawa et al.

(12) 
(10) Patent No.: US 6,187,699 B1
(45) Date of Patent: Feb. 13, 2001

(54) LAMINATED NONWOVEN FABRIC AND METHOD OF MANUFACTURING SAME

(75) Inventors: Taiju Terakawa, Yasu-gun; Shingo Horiuchi, Moriyama; Satoshi Ogata, Amagasaki, all of (JP)

(73) Assignee: Chisso Corporation, Osaka (JP)

( * ) Notice: Under 35 U.S.C. 154(b), the term of this patent shall be extended for 0 days.

(21) Appl. No.: 09/254,366

(22) PCT Filed: Jun. 5, 1997

(86) PCT No.: PCT/JP97/01913

§ 371 Date: Mar. 4, 1999

§ 102(e) Date: Mar. 4, 1999

(87) PCT Pub. No.: WO98/10130

PCT Pub. Date: Mar. 12, 1998

(30) Foreign Application Priority Data

Sep. 6, 1996 (JP) .................................................. 8-236723

(51) Int. Cl.$^7$ ................ D04H 1/00; D04H 1/16

(52) U.S. Cl. .......................... 442/382; 442/364; 442/361

(58) Field of Search ..................................... 442/361, 327, 442/364, 342, 382; 156/181, 182

(56) References Cited

U.S. PATENT DOCUMENTS 5,817,584 * 10/1998 Singer .................................. 442/561

* cited by examiner

Primary Examiner—N. Edwards
(74) Attorney, Agent, or Firm—Fay, Sharpe, Fagan, Minnich & McKee, LLP

(57) ABSTRACT

A laminated nonwoven fabric having a good texture, providing no rough touch, and having a high strength and a large delamination strength are provided.

A nonwoven fabric of a multi-layer structure comprises (a) a composite spun bonded nonwoven fabric composed of a low melting point resin component and a high melting point resin component and (b) a composite melt blown extra-fine-fiber nonwoven fabric having a fiber diameter of 10 μm or less and being composed of a low melting point resin and a high melting point resin; both of the nonwoven fabrics are laminated, and the fibers in each of the nonwoven fabrics and both of the nonwoven fabrics are thermally fused.

A method of manufacturing a nonwoven fabric having a multi-layer structure comprises laminating each of the nonwoven fabrics in a multi-layer structure and heating the laminate at a temperature higher than the thermal fusion temperature to cause thermal fusion of the both layers.

14 Claims, No Drawings

LAMINATED NONWOVEN FABRIC AND METHOD OF MANUFACTURING SAME

TECHNICAL FIELD

The present invention relates to a laminated nonwoven fabric and to a method of manufacturing the same. More specifically, the present invention relates to a nonwoven fabric of multi-layer structure comprising a composite spun bonded nonwoven fabric laminated on a composite meltblown extra-fine-fiber nonwoven fabric. The laminated nonwoven fabric is preferably used as surface material for absorptive products such as disposable diapers and sanitary napkins.

BACKGROUND ART

Spun bonded nonwoven fabrics have been used as surface material for absorptive products such as disposable diapers, because they are hardly napped or fluffed and have excellent fiber detachment resistance. However, continuous fibers (filaments or long fibers) that form the spun bonded nonwoven fabrics are difficult to make finer. Thus, the spun bonded nonwoven fabrics are difficult to provide a soft texture like that of meltblown nonwoven fabrics composed of extra-fine fibers. In addition, the spun bonded nonwoven fabrics have another drawback in that when their constituent fibers are made finer, more single fibers are cut short and thus more fibers of a larger fineness are mixed, leading to deterioration in texture.

Laid-open Japanese Patent Publication No. Sho 54-134177 discloses a meltblown nonwoven fabric composed of extra-fine polypropylene fibers, and Laid-open Japanese Patent Publication Nos. Sho 62-299501 and Hei 3-75056 disclose a disposable diaper employing a meltblown nonwoven fabric as its surface material. Meltblown nonwoven fabrics are advantageous in that they provide a soft texture due to their small fiber diameter. However, meltblown nonwoven fabrics have inherent drawbacks, including weak nonwoven fabric strength, generation of naps or fluffs, and tendency of permitting fiber detachment. In addition, they have such drawbacks that polymer particles are likely to be formed at the time of spinning, thus imparting the fabrics rough hand feeling, and the fabrics irritate the skin, making it unsuitable for disposable diapers for newborn babies. In order to improve the strength of meltblown nonwoven fabrics and to prevent fiber detachment, the meltblown nonwoven fabrics are being subjected to pressing with heated calender rolls or heated emboss rolls. However, the heat pressing must be performed under severe temperature and pressure conditions, leading to increase in the apparent density of the nonwoven fabrics and deterioration in the texture thereof.

Japanese Patent Publication No. Sho 60-11148 and Laid-open Japanese Patent Publication Nos. Hei 2-112458 and Hei 2-234967 disclose a laminated nonwoven fabric wherein a spun bonded nonwoven fabric is laminated on a meltblown nonwoven fabric, and the two layers are thermally fused to each other by the use of heated calender rolls, heated emboss rolls, or the likes. The resultant nonwoven fabric has improved strength as compared with that of conventional single-layer nonwoven fabrics. However, the nonwoven fabric has drawbacks, including unsatisfactory fusion between layers, poor fiber detachment resistance, and insufficient delamination strength, since regular fibers are used as continuous fibers that compose the spun bonded nonwoven fabric. In addition, in order to press the spun bonded nonwoven fabrics with heated emboss rolls, severe heating and pressing conditions are required, leading to drawbacks such as high apparent density and deterioration in texture.

DISCLOSURE OF THE INVENTION

An object of the present invention is to provide a laminated nonwoven fabric which has a high strength, soft texture, and excellent fiber detachment resistance, is not rough to the touch, and causes no irritation to the skin. Another object of the present invention is to provide a method of manufacturing the laminated nonwoven fabric.

The present invention for achieving the above objects is summarized as follows:

(1) A laminated nonwoven fabric of multi-layer structure comprising a composite spun bonded nonwoven fabric laminated on a composite meltblown extra-fine-fiber nonwoven fabric having an average fiber diameter of 10 μm or less; wherein the composite spun bonded nonwoven fabric comprises a composite continuous fiber composed of a low melting point resin and a high melting point resin, the difference in melting point between the low melting point resin and the high melting point resin being at least 10° C., the low melting point resin forming at least a portion of the surface of the fiber, and the composite spun bonded nonwoven fabric being a partial thermal fusion product of the composite continuous fibers by the mediation of the low melting point resin, the composite meltblown extra-fine-fiber nonwoven fabric comprises composite meltblown extra-fine fibers composed of a low melting point resin and a high melting point resin, the difference in melting point between the low melting point resin and the high melting point resin being at least 10° C., the low melting point resin forming at least a portion of the surface of the fiber, and the composite meltblown extra-fine-fiber nonwoven fabric being a partial thermal fusion product of the extra-fine fibers by the mediation of the low melting point resin; and the composite spun bonded nonwoven fabric and the composite melt-blown extra-fine-fiber nonwoven fabric are integrated by fusion of the low melting point resin of the composite spun bonded nonwoven fabric and/or the low melting point resin of the composite meltblown extra-fine-fiber nonwoven fabric.

(2) A laminated nonwoven fabric as described in (1), wherein the composite spun bonded nonwoven fabric comprises composite continuous fibers having a fineness of 0.5–10 d/f, the composite meltblown extra-fine-fiber nonwoven fabric comprises extra-fine fibers having a fiber diameter of 0.1–10 μm, has 10/m$^2$ or less of polymer particles having a diameter of at least 0.1 mm, and has an apparent density of 0.02–0.20 g/cm$^3$; and the laminated nonwoven fabric has a strength in the lateral direction of 0.6 kg/5 cm or more, uniformity index of 0.6 or less, and a delamination strength between the two layers of 6 g/5 cm or more.

(3) An absorptive product comprising a laminated nonwoven fabric as described in (1) or (2) as at least one component of the product.

(4) An absorptive product as described in (3) wherein the product comprises a nonwoven fabric of double-layer structure composed of a composite spun bonded nonwoven fabric and a composite meltblown extra-fine-fiber nonwoven fabric; or a nonwoven fabric of multi-layer structure comprising at least three layers, composed of a composite spun bonded nonwoven fabric and a composite meltblown extra-fine-fiber nonwoven fabric, and having the composite meltblown extra-fine-fiber nonwoven fabric laminated on at least one side of the laminated nonwoven fabric.

(5) A method of manufacturing a laminated nonwoven fabric comprising the steps of:

spinning composite continuous fibers from a low-melting point resin and a high melting point resin so that at least a portion of the fiber surface is formed by the low-melting point resin, the difference in melting point between the low melting point resin and the high melting point resin being at least 10° C., and forming a spun bonded web by a composite spun bonding method; or heating the resultant fiber web at a temperature not lower than a thermal fusion temperature thereby to form a nonwoven fabric in which some parts of the fibers are thermally fused;

spinning composite meltblown extra-fine-fibers having an average fiber diameter of 10 μm or less, and comprising a low-melting point resin and a high melting point resin, the difference in melting point between the low melting point resin and the high melting point resin is at least 10° C., in such a fashion that the low-melting point resin forms at least a portion of the fiber surface, and forming a composite extra-fine-fiber web which does not include thermally fused portions by self-heating at the time of spinning, or forming a nonwoven fabric which includes portions thermally fused by self-heating at the time of spinning by a composite melt-blowing method; or forming a composite extra-fine-fiber nonwoven fabric in which some of the fibers are thermally fused by heating the spun fiber web or the nonwoven fabric which includes thermally self-fused portions at a temperature not lower than a thermal fusion temperature;

laminating the spun bonded web or the thermally fused nonwoven fabric, and the composite melt-blown extra-fine-fiber web or a composite melt-blown extra-fine-fiber thermally-fused nonwoven fabric; and heating the resultant laminate at a temperature not lower than the temperature at which the two layers become thermally fused.

(6) A method of manufacturing a laminated nonwoven fabric as described in (5) wherein the method further comprises a step of causing entanglement of the fibers in the webs or nonwoven fabrics of the two layers by a needle-punch or spun lace means before or after heating.

(7) A method of manufacturing a laminated nonwoven fabric as described in (6) wherein the laminate is heated with a through-air type heater at least at a thermal fusion temperature of the two layers.

(8) A method of manufacturing a laminated nonwoven fabric as described in (5) or (6) wherein the two layers are press-bonded under heating by the use of emboss rolls having a thermal press-bonding area of 5–25%.

(9) A method of manufacturing a laminated nonwoven fabric as described in (5) or (6) wherein the composite spun-bonded nonwoven fabric and the composite melt-blown extra-fine-fiber nonwoven fabric each having a uniformity index of 0.6 or less are used as nonwoven fabric.

(10) A method of manufacturing a laminated nonwoven fabric as described in (5) or (6) wherein the two layers are heated with an alternatively hot-air jetting heater such that hot air is jetted from the top face side and the bottom face side of the nonwoven fabric of multi-layer structure in an alternating manner.

As the nonwoven fabric of multi-layer structure of the present invention, any fabric can be used so long as it is a nonwoven fabric having a structure of at least two layers in which a composite spun bonded nonwoven fabric and a composite meltblown extra-fine-fiber nonwoven fabric are laminated. For application as wiping cloths or surface material for disposable diapers, a nonwoven fabric having 2 or 3 layers can be used, and for application as heat insulating material or material for preventing moisture condensation, a nonwoven fabric having 2 to 8 layers can be used.

The composite spun bonded nonwoven fabric used in the nonwoven fabric having a multi-layer structure of the present invention is produced from at least two resin components having a difference in melting points by at least 10° C. by a composite spun bonding method and the fibers therein are thermally fused to one another at the junctions thereof. A composite spun bonding method is a method of manufacturing a thermally fused nonwoven fabric that comprises the following steps: A plurality of resin components are melt extruded from a plurality of extruders. The plurality of the resin components are extruded from a composite spinning nozzle to form continuous fibers such that a low melting point resin component forms at least a part of the fiber surface. The thus-obtained fibers are aspirated by an airflow suction apparatus such as an air sucker, and then collected together with airflow by a web collecting apparatus such as a net conveyer. If necessary, the thus-obtained web is subjected to a treatment such as fusion by the use of a heating apparatus using heated air or heating rolls.

There may be employed another method of manufacturing a nonwoven fabric, wherein spun continuous fibers are mechanically stretched, subsequently aspirated by an airflow suction apparatus such as an air sucker as mentioned above, then collected together with airflow by a web collecting apparatus such as a net conveyer, and finally subjected to thermal fusion as in the case described above. In practice, two to four resin components may be used as the resin components, and no limitation is imposed on the resin components so long as the difference between the highest melting point and the lowest melting point of these resin components is at least 10° C. Use of two resin components is sufficient for most applications.

The nonwoven fabric preferably has a uniformity index of basis weight, which will be described below, of 0.6 or less. Unification of basis weight can be achieved by selecting a composite spun-bonding machine or setting the spinning conditions and the like by trial and error.

No limitation is imposed on the resins used in the present invention so long as they are spinnable thermoplastic resins. Examples of resins that can be used in the present invention include polyolefins such as polypropylenes, high-density polyethylenes, mid-density polyethylenes, low-density polyethylenes, linear low-density polyethylenes, and binary or ternary copolymers of propylene and another α-olefin; polyamides; polyesters such as polyethylene terephthalates, polybutene terephthalates, low melting point polyesters obtained through copolymerization of a diol and terephthalic acid/isophthalic acid or the likes, and polyester elastomers; fluorine plastics; mixtures of the resins described above; and other spinnable resins.

Examples of the combination of the resins at the time of composite spinning include high-density polyethylene/polypropylene, low-density polyethylene/propylene-ethylene-butene-1 crystalline copolymer, high-density polyethylene/polyethylene terephthalate, Nylon 6/Nylon 66, low melting point polyester/polyethylene terephthalate, polypropylene/polyethylene terephthalate, polyvinylidene fluoride/polyethylene terephthalate, and a mixture of linear low-density polyethylene and high-density polyethylene/polypropylene.

Examples of the form or morphology of the composite fibers include sheath-core, side-by-side, multi-layer, hollow multi-layer, and not-circular multi-layer type. Also, it is sufficient that the low melting point resin component described above forms at least a part of the surface of the fibers. The difference in melting point between a high melting point resin and a low melting point resin is necessary to be at least 10° C. When the difference is less than 10° C., (a) the temperature is difficult to control when heat treatment is performed during manufacture of the composite spun bonded nonwoven fabric or a laminated nonwoven fabric wherein the composite spun bonded nonwoven fabric is laminated on a composite meltblown extra-fine-fiber nonwoven fabric, or (b) thermal fusion is insufficient and thus a nonwoven fabric having a sufficient strength can not be obtained. Alternatively, wrinkles may be produced on the nonwoven fabric by heating at an excessively high temperature and/or whole of the nonwoven fabric melts to form a nonwoven fabric in which a portion of the fabric has a film-like texture. Also, the thus-obtained laminated nonwoven fabric may have insufficient fiber detachment resistance or may readily be peeled off at laminated surfaces.

The composite ratio of the low melting point resin to the high melting point resin in the composite spun bonded continuous fibers is 10 to 90% by weight for the low-melting point resin and 90 to 10% by weigh for the high-melting point resin. More preferably, it is 30 to 70% by weight for the low-melting point resin and 70 to 30% by weight for the high-melting point resin. When the amount of the low melting point resin is less than 10% by weight, thermal fusion of the composite spun bonded nonwoven fabric itself becomes insufficient or thermal fusion between the nonwoven fabric and the composite meltblown extra-fine-fiber nonwoven fabric at laminated surfaces becomes insufficient, thereby to produce a nonwoven fabric of insufficient strength and insufficient fiber detachment resistance.

The fineness of the composite continuous fibers is not particularly limited. However, it is about 0.2 to 10 d/f in the case of the surface material for disposable diapers, and about 0.5 to 20 d/f in the case of wipers, and about 0.2 to 4000 d/f in the case of filters. While the basis weight of the nonwoven fabric is not particularly limited, it falls within the range of about 4–1000 g/m². In the case of the surface material for disposable diapers, it is about 4 to 70 g/m²; in the case of wipers or the likes, it is about 10 to 600 g/m²; and in the case of filters, it is about 20 to 1000 g/m².

Composite spun bonded nonwoven fabrics having a higher strength can be obtained by using a heater such as a air-through type heater, heated calender rolls, or heated embossing rolls. In the present invention, it is preferable to increase the strength of the nonwoven fabric alone to at least 0.6 kg/5 cm by using the aforementioned heater and controlling heating conditions and others.

The composite meltblown extra-fine-fiber nonwoven fabric used in the present invention is a nonwoven fabric obtained by the method as follows: At least two thermoplastic resins whose melting points differ from each other by at least 10° C. are separately melt extruded. A low-melting point resin and a high-melting point resin are extruded from a composite-type melt blow spinning nozzle so that the low-melting point resin forms at least a part of the fiber surface, and formed into streams of extra-fine-fiber with a high temperature and high velocity gas by blow spinning, formed into a composite extra-fine-fiber web with a collecting apparatus, and subjected to a heat fusing treatment, when necessary.

It is sufficient that a low-melting point resin forms at least a part of the fiber surface in the composite melt-blown extra-fine-fibers of the present invention. The composite ratio is preferably 10 to 90% by weight for the low-melting point resin and 90 to 10% by weight for the high-melting point resin. It is sufficient that the form of composite fibers is sheath-core, side-by-side as in the case of spun bonding described above.

As the resins, a variety of resins used for the aforementioned composite spun bonding can also be used. As the combination of resins, various combinations of resins as disclosed with reference to the composite spun bonding are possible. Examples of the combinations include high-density polyethylene/polypropylene, propylene-ethylene-butene-1 crystalline copolymer, high-density polyethylene/polyethylene terephthalate, and low melting point polyester/polyethylene terephthalate.

As the gas used at the time of blow spinning, an inert gas such as air and nitrogen gas is usually used. The temperature of the gas is about 200–500° C., preferably about 250–450° C., and the pressure is about 0.1–6 kg/cm², preferably about 0.2–5.5 kg/cm². These spinning conditions can suitably be selected according to the properties and combination of the resins to be used, intended fiber diameter, apparatuses including spinning nozzles to be used, and the likes.

The nonwoven fabric is composed of composite extra-fine-fibers having an average fiber diameter of 10 $\mu$m or less. The average fiber diameter is preferably 0.1–9 $\mu$m and more preferably 0.2–8 $\mu$m. When the fiber diameter exceeds 10 $\mu$m, the texture of the web is deteriorated. However, the web having a fiber diameter of 0.1 $\mu$m or less is difficult to manufacture and their price becomes expensive.

Meltblown nonwoven fabrics used in the present invention are those wherein the number of polymer particles is 10/m² or less. The word "polymer particles" used herein means such ones as having a non-fibrous shape such as a round, oval, or tear-drop shape, and having a diameter of at least 0.1 mm. When the number of the polymer particles increases, the fabric has a rough texture and irritates the skin, even if the fabric feels soft to the touch. Therefore, such a fabric can not be used as material that comes in direct contact with the skin, for instance, it can not be used as a surface material for disposable diapers and a substrate for cataplasm. Both surfaces of wiping cloths for eyeglasses, furniture, etc. are preferably made of meltblown nonwoven fabric. However, such wiping cloths may sometimes exhibit a disadvantage of scratching furniture and the like in addition to the rough texture described above.

In the present invention, the nonwoven fabrics having a uniformity index of basis weight of 0.6 or less are preferably used. Such nonwoven fabrics can be obtained by selecting suitable spinning conditions for composite melt blow spinning and appropriate apparatuses.

The fibers of a composite meltblown extra-fine-fiber nonwoven fabric used in the present invention are thermally fused to one another at the junctions thereof. The thermal fusion may be performed by self-heating at the time of spinning, or by using a heater such as a heated air-through type heater, heated calender rolls, or heated emboss rolls at a step after spinning. While the basis weight of the nonwoven fabric is not particularly limited, it is in the range of about 3–1000 g/m². The basis weight of the nonwoven fabric is about 3–60 g/m² in the case of the surface material for disposable diapers, about 5–500 g/m² in the case of wiping cloths, and about 15–1000 g/m² in the case of filters. The apparent density of the nonwoven fabrics is not particularly limited, but preferably falls within the range of about 0.02–0.40 g/cm³ from consideration of their texture.

The laminated nonwoven fabrics of the present invention can be manufactured by laminating a composite spun bonded nonwoven fabric and a composite meltblown nonwoven fabric described above, and then heating the laminated fabric by the use of a heater such as a heated through-air type heater, an alternatively heated-air jetting type heater, heated calender rolls, heated emboss rolls, or a sonic bonding apparatus to cause thermal fusion of the two layers. When a heated through-air type heater or an alternatively heated-air jetting type heater is used, there is obtained a relatively bulky meltblown nonwoven fabric. When a heated through-air type heater is used, the delamination strength between the layers can be increased by heating the fabrics so that the heat penetrates first from the side of the spun bonded nonwoven fabric, which has a relatively large fineness, to the side of the meltblown nonwoven fabric, which has a small fineness, since the heat is applied uniformly to the fabrics. When the laminated nonwoven fabric is heated with a through-air type heater with the side of the meltblown nonwoven fabric being faced to a heated air outlet of the heater, the delamination strength between the two layers can be controlled by selecting suitable heated air pressure, suction conditions, and others, since single meltblown extra-fine fibers come to be entangled in the spun bonded nonwoven fabric layer and thermally fused twice within the spun bonded nonwoven fabric and in the both layers. A bulky nonwoven fabric can also be obtained even when a heater which jets heated air alternately to the front side and back side of the nonwoven fabric is used. A laminated nonwoven fabric having a high delamination strength can be obtained by laminating both nonwoven fabrics, subjecting the laminated fabric to an entangling treatment, for example, by a needle punch method or a spun lace method, followed by a heating treatment. It is sufficient that the heating temperature is higher than the softening temperature of a low-melting point resin component of the composite continuous fiber composing a composite spun bonded nonwoven fabric or higher than the softening temperature of the low-melting point resin of the composite meltblown nonwoven fabric. When both of the two layers are heated, thermal fusion of fibers of either nonwoven fabric or both of the fabrics can also be performed at the same time. When a thermally fused composite spun bonded nonwoven fabric is rolled, unrolled, and then heated, it is sufficient that the heating temperature is higher than the softening temperature of the low-melting point resin of the meltblown nonwoven fabric. When it is heated at a temperature higher than the softening or thermal fusing temperature of the low-melting point resin component of the both composite spun bonded fabric and the meltblown nonwoven fabric, a laminated nonwoven fabric having a high delamination strength can be obtained. When it is heated with heated emboss rolls, it is preferable to make the area of heat pressing to 5–25%. When the thermal press-bonding area is less than 5%, detachment resistance and strength of nonwoven fabric become poor. When the heat presing area exceeds 25%, the texture of the thus-obtained fabric becomes hard.

In the present invention, it is preferable to make the delamination strength of the both layers higher than 6 g/5 cm by selecting proper heating conditions, a low melting point resin of the composite spun bonded nonwoven fabric, a low melting point resin of the composite meltblown extra-fine-fiber nonwoven fabric, and the likes. The delamination strength is 6–5000 g/5 cm, and more preferably about 10–4000 g/5 cm. When the delamination strength is less than 6 g/5 cm, both of the layers are easily delaminated by friction, etc., thus making the laminated fabric unsuitable for disposable diapers or the like products. When the same resin is used for both of the low-melting point resin of the composite spun bonded nonwoven fabric and the low-melting point resin of the composite meltblown extra-fine fiber, there can be obtained a laminated fabric of extremely high delamination strength.

Since the laminated nonwoven fabric of the present invention employs a high strength of a composite spun bonded nonwoven fabric, composite spun bonded nonwoven fabrics having a strength in the lateral direction of 0.6 kg/5 cm or higher as reduced to that of a nonwoven fabric having a basis weight of 40 g/m$^2$ are preferable. The lateral direction used herein refers to a so-called cross-machine direction (CD) of a spun bonded nonwoven fabric layer. When the laminated fabric has multi-layers, the strength in the lateral direction refers to the lesser of the longitudinal strength and the lateral strength. When the apparent density of laminated meltblown nonwoven fabrics after lamination is assumed to be 0.02–0.20 g/cm$^3$, it is particularly preferred, because a soft texture of extra-fine-fibers of such a meltblown nonwoven fabric can be employed for various uses, e.g. surface material for disposable diapers. The apparent density is about 0.02 to 0.20 g/cm$^3$ in the case for wiping cloths or surface material for disposable diapers, and 0.025–0.40 g/cm$^3$ in the case of filters or the like.

The laminated nonwoven fabrics of the present invention preferably has a uniformity index of basis weight of 0.6 or less. Such nonwoven fabrics can be obtained by using a composite spun bonded nonwoven fabric and a composite meltblown extra-fine-fiber nonwoven fabric each having a uniformity index of basis weight of 0.6 or less.

The laminated nonwoven fabrics of the present invention can be used, singly or after being laminated with, sewed to, or thermally fused to another material, for various uses. For instance, when the laminated nonwoven fabrics are used as a material for underpants-shaped disposable diapers, they can be used in areas where a relatively high water repellency is required; for example, as liner material used in the vicinity of the trunk and legs. When such diapers have a narrow strip of a vertical blocking layer in the vicinity of the legs for prevention of leakage of liquid, the laminated nonwoven fabric can also be used as material for such vertical blocking layers after thermally fused to another material. When the laminated nonwoven fabric is used in such a diaper, an elastic material can be used in combination with another material or the laminated nonwoven material so that the diapers are brought into close contact with the trunk and the legs. Further, the laminated nonwoven material can also be used as covering material for an underpants-shaped disposable diapers with the layer of a composite meltblown extra-fine-fiber nonwoven fabric being placed outside or inside. Still further, the laminated nonwoven fabric can also be used as covering material for the aforementioned surface material and as covering material for the liner material described above after laminated on another nonwoven fabric, tissue, web, film, or the like.

The laminated nonwoven fabric can be used as a material for forming a part of the aforementioned surface material or liner material by disposing a large number of permeation holes of about 0.1–9 mm$^2$ in a nonwoven fabric of any one of the layers of a laminated nonwoven fabrics and/or the entire laminated nonwoven fabric so that liquid and moisture permeate quickly. Further, the multi-layer nonwoven fabric may be applied with a finishing agent (or oiling agent) such as a water repellent finishing agent and hydrophilic finishing agent, or a fluorine-containing water repellent agent for controlling the permeability.

The multi-layer nonwoven fabrics of the present invention can be laminated, for example, in such a sequence as meltblown nonwoven fabric/spun bonded nonwoven fabric/meltblown nonwoven fabric, applied with a variety of lubricants, and can be used for wipers for furniture or the likes.

The laminated nonwoven fabrics may be processed into filtering material after being pleated, molded into a cylindrical (or tubular) shape, molded into a cylindrical shape by winding as they are; or molded into a cylindrical shape while being heated so that the layers are thermally fused to one another.

BEST MODE FOR CARRYING OUT THE INVENTION

Now, the present invention will be described in more detail with reference to Examples. In the Examples, evaluation of nonwoven fabrics was carried out as follows:

Fiber diameter: Ten small pieces were cut away from a web or nonwoven fabric, a photograph of 100 to 5000 magnification was taken by using a scanning type electron microscope, and diameter of 100 sample fibers were determined. Average value was assumed to be the fiber diameter (unit: $\mu$m).

Tensile strength of nonwoven fabric: Vertical breaking strength and lateral breaking strength (kg/5 cm) of a non-woven fabric having a width of 5 cm were determined by using a tensile strength tester. The average value of five measurements was assumed to be the tensile strength.

Texture: Five panelists evaluated the texture (or hand feeling) of a sample nonwoven fabric in terms of wrinkling, flexibility, and roughness to the touch (rough feel). The judgment was made according to the following standards. When three or more of the panelists judged that the sample had no wrinkling, had a high flexibility, and had no rough feel, the texture was decided to be "good," and when three or more panelists judged that the sample had wrinkles, poor flexibility, or rough feeling, or any combination of two or more of these properties, the texture was decided to be "poor."

Polymer particle: Ten sheets of nonwoven fabrics each having a size of 20×20 cm were cut away at random, and the number of polymer particles (unit: number/m$^2$) having a diameter larger than 0.1 mm were counted by using a magnifying glass.

Fiber detachment: A sheet of nonwoven fabric having a size of 20×20 cm was cut away and placed on a horizontal surface. A person in charge of the evaluation lightly press the surface of the nonwoven fabric with a wet hand, and rub the surface of the fabric so as to draw a circle continuously five times. Subsequently, the person check the hand for the presence or absence of detached fibers. When detached fibers were present on the hand, the fiber detachment was assumed to be "presence," and when no detached fibers were present, the detachment was assumed to be "absence."

Delamination strength: A piece of laminated nonwoven fabric having a width of 5 cm was cut away. One layer was peeled from the other layer while cutting fabric at the laminated surfaces by using a razor. Delamination strength was determined by the use of a tensile strength tester. The average value of five measurements was assumed to be the delamination strength (unit: g/5 cm).

Uniformity index of average basis weight of nonwoven fabric: 40 samples having a size of 5 cm×5 cm were cut out from a laminated nonwoven fabric at random. The basis weight (g/m$^2$) of each sample was measured. The uniformity index of average basis weight was calculated from the following formula.

$$\text{Uniformity index} = (\text{maximum basis weight} - \text{minimum basis weight})/\text{average basis weight}.$$

EXAMPLE 1

A thermally fused composite nonwoven fabric was prepared by the use of a composite-spun-bonding machine equipped with a composite spinning machine, an air sucker, a net-conveyor, and a heater. Sheath-core type composite-spinning nozzles having an orifice diameter of 0.4 mm were used. High-density polyethylene having a melting point of 133° C. and an MFR of 22 (190° C., g/10 minutes) was used on the sheath side as the first component, and polypropylene having a melting point of 164° C. and an MFR of 60 (230° C., g/10 minutes) was used on the core side as the second component. These polymers were spun at a composite ratio of 50/50 (% by weight), a spinning temperature of 285° C. for the first component, and a spinning temperature of 300° C. for the second component, and then aspirated by the use of an air sucker at a velocity of 3000 m/minute. The resultant fibers were blown on the net-conveyor together with air. The blown air was aspirated and removed by the use of an aspirating exhaustion apparatus installed under the net-conveyor. The resultant web had a fineness of 1.5 d/f. The web was heated at 145° C. by the use of a through-air type heater to obtain a nonwoven fabric in which the fibers were joined by thermal fusion. The nonwoven fabric had a basis weight of 18 g/m$^2$, uniformity index of 0.25, vertical strength of 2.97 kg/5 cm, and lateral strength of 1.75 kg/5 cm.

A composite meltblown extra-fine-fiber nonwoven fabric was prepared by the use of a melt-blow-spinning machine equipped with side-by-side type composite-melt-blow spinning nozzles having an orifice diameter of 0.3 mm, a net conveyor, etc. Propylene-ethylene-butene-1 terpolymer having a melting point of 135° C. and an MFR of 76 (190° C., g/10 minutes) was spun as the first component at a spinning temperature of 280° C., and polypropylene having a melting point of 166° C. and an MFR of 82 (230° C., g/10 minutes) was spun as the second component at a spinning temperature of 290° C. at a composite ratio of 50/50 (% by weight). The spun fibers were blown to the net-conveyor by blowing heated air under conditions of air temperature of 360° C. and a pressure of 1.5 kg/cm$^2$. The blown air was aspirated and removed by the use of an aspirating exhaustion apparatus installed under the net-conveyor. The resultant web had a fiber diameter of 1.8 $\mu$m. The web was heated at 135° C. by the use of a through-air type heater to obtain a nonwoven fabric wherein fibers were joined at junctions through thermal fusion of the low melting point extra-fine fibers.

The nonwoven fabric had a basis weight of 20 g/m$^2$, uniformity index of 0.14, vertical strength of 1.72 kg/5 cm, lateral strength of 0.89 kg/5 cm, and apparent density of 0.055 g/cm$^3$.

The composite spun bonded nonwoven fabric and the composite meltblown nonwoven fabric were laminated and heated at 142° C. by the use of a through-air heater to obtain a laminated nonwoven fabric of two-layer structure in which the two layers were thermally fused in part. The heat treatment was carried out in such a way that hot air was jetted from the side of the composite spun bonded fabric to the side of the composite meltblown extra-fine fibers. The laminated nonwoven fabric slightly increased in its basis weight to 40 g/m$^2$ by the heat treatment performed after lamination. The laminated nonwoven fabric had a uniformity index of 0.18, vertical strength of 7.26 kg/5 cm, and lateral strength of 5.33 kg/5 cm. Apparent density of the meltblown nonwoven fabric which was separated by cutting the laminated nonwoven fabric along the bonded surfaces by the use of a razor slightly increased to 0.059 g/cm$^3$ by the heat treatment after lamination.

The laminated nonwoven fabric had a good texture, no fiber detachment, no polymer particles, and a delamination strength of 149 g/5 cm.

EXAMPLE 2

A composite meltblown extra-fine-fiber nonwoven fabric was prepared by the same preparation method as in Example 1. However, sheath-core type, composite-melt-blow spinning nozzles having an orifice diameter of 0.3 mm were used. Treatment by the air-through type heater was not carried out. Linear low density polyethylene having a melting point of 122° C. and an MFR of 122 (190° C., g/10 minutes) was spun as the first component at a spinning temperature of 260° C., and polypropylene having a melting point of 165° C. and an MFR of 120 (230° C., g/10 minutes) was spun as the second component at a composite ratio of the first component to the second component of 40/60 (% by weight) and a spinning temperature of 280° C., followed by blowing of heated air under conditions of heated air temperature of 370° C. and a pressure of 1.9 kg/cm$^2$ to blow the spun fibers onto the net-conveyor. The resultant web had a fiber diameter of 3.1 μm. The web had a structure like a nonwoven fabric having thermally fused portions at junctions of the fibers caused by the self-heating at the time of spinning. The resultant nonwoven fabric had a basis weight of 17 g/m$^2$, uniformity index of 0.30, vertical strength of 0.86 kg/5 cm, lateral strength of 0.61 kg/5 cm, and apparent density of 0.043 g/cm$^3$.

The composite spun bonded nonwoven fabric obtained in Example 1 and the composite meltblown nonwoven fabric described above which has thermally fused portions caused by the self-heating, but was not subjected to a heat treatment were laminated and heated at 135° C., as in Example 1, to obtain a laminated nonwoven fabric of two-layer structure in which two layers were thermally fused to each other. The heat treatment was carried out with the composite meltblown nonwoven layer facing to the side from which heated air was jetted. Basis weight of the laminated nonwoven fabric was slightly increased to 36 g/m$^2$ by the heat treatment. The laminated nonwoven fabric had a uniformity index of 0.28, vertical strength of 4.01 kg/5 cm, and lateral strength of 3.18 kg/5 cm. Apparent density of the meltblown nonwoven fabric which was determined after cutting the laminated nonwoven fabric with a razor at the laminated faces to separate them was slightly increased to 0.046 g/cm$^3$ by the heat treatment after lamination.

The laminated nonwoven fabric had a good texture, no fiber detachment, and no polymer particles, and its delamination strength was 102 g/5 cm.

COMPARATIVE EXAMPLE 1

A meltblown nonwoven fabric was prepared by the same preparation method as in Example 1. However, heat treatment by the air-through type heater after spinning was not carried out. Melt-blow spinning nozzles for regular fiber having an orifice diameter of 0.3 mm were used. Polypropylene having a melting point of 167° C. and an MFR of 21 (230° C., g/10 minutes) was spun at a spinning temperature of 300° C., followed by blowing of heated air under conditions of heated air temperature of 360° C. and a pressure of 1.5 kg/cm$^2$ to obtain an extra-fine-fiber web. The resultant web had a fiber diameter of 8.9 μm. The web was a nonwoven fabric like product having thermally fused portions at junctions of the fibers by the self-heating caused at the time of spinning. The nonwoven fabric had a basis weight of 18 g/m$^2$. The nonwoven fabric was found to have polymer particles by visual and tactile inspection. The nonwoven fabric had a uniformity index of 0.32, vertical strength of 0.88 kg/5 cm, lateral strength of 0.75 kg/5 cm, and apparent density of 0.070 g/cm$^3$.

Polyethylene terephthalate spun bonded nonwoven fabric having a fineness of 2.6 d/f, basis weight of 20 g/m$^2$, uniformity index of 0.08, vertical strength of 4.33 kg/5 cm, and lateral strength of 3.01 kg/5 cm and the meltblown nonwoven fabric described above were laminated and heated at 158° C. as in Example 1 to obtain a laminated nonwoven fabric of two-layer structure in which the two layers were thermally fused slightly. The spun bonded nonwoven fabric mentioned above was a product which was thermally fused in part by heated emboss rolls. The resultant laminated nonwoven fabric slightly increased in basis weight to 40 g/m$^2$ by the heat treatment of the laminated product. The laminated nonwoven fabric had a uniformity index of 0.64, vertical strength of 6.85 kg/5 cm, and lateral strength of 4.27 kg/5 cm. Apparent density of the meltblown nonwoven fabric which was determined after separating the laminated faces was slightly increased to 0.084 g/cm$^3$ by the heat treatment after lamination. In the laminated nonwoven fabric, wrinkles in the wave form were generated in the meltblown nonwoven fabric.

The laminated nonwoven fabric had no fiber detachment. The laminated nonwoven fabric was poor in flexibility, and had a rough texture and irritation to the skin due to the presence of polymer particles. The fabric also had 26 polymer particles per square meter and a delamination strength of 5 g/5 cm.

COMPARATIVE EXAMPLE 2

A composite meltblown extra-fine-fiber nonwoven fabric was prepared by the same preparation method as in Example 1. However, heat treatment was not carried out after spinning. The same resins as in Example 1 were used as the first component and the second component, and the composite ratio of the components was also 50/50 (% by weight). Both the first and the second components were spun at 250° C., followed by blowing heated air under conditions of a heated air temperature of 250° C. and a pressure of 0.8 kg/cm$^2$ to obtain an extra-fine-fiber web. The resultant web had a fiber diameter of 18.9 μm. The web had a nonwoven fabric like structure in which fibers were thermally fused at their junctions by the self-heating at the time of spinning. The nonwoven fabric had a basis weight of 16 g/m$^2$ and uniformity index of 0.13. The nonwoven fabric had a vertical strength of 0.91 kg/5 cm, lateral strength of 0.52 kg/5 cm, and apparent density of 0.065 g/cm$^3$.

The composite spun bonded nonwoven fabric obtained in Example 1 and the meltblown nonwoven fabric described above were laminated and heated at 140° C., as in Example 1, to obtain a laminated nonwoven fabric of two-layer structure in which the two layers were thermally fused in part. The laminated nonwoven fabric slightly increased in basis weight to 35 g/m$^2$ by the heat treatment of the laminated product. The laminated nonwoven fabric had a uniformity index of 0.24, vertical strength of 4.14 kg/5 cm, and lateral strength of 3.01 kg/5 cm. Apparent density of the meltblown nonwoven fabric determined after cutting the laminated nonwoven fabric at the laminated faces with a razor to separate was slightly increased to 0.068 g/cm³ by the heat treatment after lamination.

The laminated nonwoven fabric had no fiber detachment, no polymer particles, and delamination strength of 61 g/5 cm. However, the laminated nonwoven fabric had a hard, poor texture because the fibers which form the meltblown nonwoven fabric had a large fiber diameter.

EXAMPLE 3

A composite spun bonded nonwoven fabric was prepared by the same preparation method as in Example 1. However, propylene-ethylene-butene-1 terpolymer having a melting point of 135° C. and an MFR of 76 (230° C., g/10 minutes) was used as the first component on the sheath side; polyethylene terephthalate having a melting point of 257° C. was used as the second component on the core side; these polymers were spun under conditions of a composite ratio of 50/50 (% by weight), a spinning temperature of 280° C. for the first component and a spinning temperature of 295° C. for the second component; aspirated by an air sucker at a velocity of 2647 m/minute; and the resultant fibers were blown onto a net-conveyor together with air. The resultant web had a fineness of 1.7 d/f. The web was heated at 152° C. with a through-air type heater to obtain a nonwoven fabric in which the fibers were thermally fused to each other in part. The nonwoven fabric had a basis weight of 23 g/m², uniformity index of 0.22, a vertical strength of 4.26 kg/5 cm, and lateral strength of 3.81 kg/5 cm.

A composite meltblown extra-fine-fiber nonwoven fabric was prepared in the same manner as in Example 1. However, heat treatment was not carried out after spinning; sheath-core-type spinning nozzles having an orifice diameter of 0.3 mm were used; the same terpolymer as used in Example 1 was used as the first component on the sheath side and polypropylene having a melting point of 166° C. and an MFR of 74 (230° C., g/10 minutes) was used as the second component on the core side; and these polymers were spun at a spinning temperature of 280° C. for both the first component and the second component wherein the composite ratio of the first component to the second component was 40/60 (% by weight); the temperature of the heated air was 380° C., and the pressure was 2.3 kg/cm². The resultant nonwoven fabric had a fiber diameter of 2.6 μm and basis weight of 20 g/m². The nonwoven fabric was a product in which fibers are weakly fused by the self-heating at the time of spinning. The nonwoven fabric had a uniformity index of 0.34, vertical strength of 0.54 kg/5 cm, lateral strength of 0.48 kg/5 cm, and apparent density of 0.061 g/cm³.

The resultant composite spun bonded nonwoven fabric and composite meltblown nonwoven fabric were laminated one on another and subjected to one step of a treatment for fiber entanglement with small columnar water streams by using a spun lacing apparatus under a condition of a pressure of 70 kg/cm². Then, the fabrics were heated at 150° C. as in Example 1 to obtain a laminated nonwoven fabric of two-layer structure in which two layers were thermally fused. The multi-layer nonwoven fabric was slightly decreased in basis weight to 37 g/m² by the spun lacing treatment or the heat treatment of the laminated product. The laminated nonwoven fabric had a uniformity index of 0.13, vertical strength of 6.03 kg/5 cm, and lateral strength of 5.02 kg/5 cm. Apparent density of the meltblown nonwoven fabric determined after cutting the laminated nonwoven fabric at the laminated faces with a razor to separate them was slightly increased to 0.092 g/cm³ by the spun lacing treatment after lamination and heat treatment.

The laminated nonwoven fabric had a good texture and no fiber detachment. The fabric had no polymer particles and a delamination strength of 405 g/5 cm.

EXAMPLE 4

The laminated nonwoven fabric of two-layer structure in which two layers were thermally fused in part, and which was prepared in Example 2 was laminated again such that the spun bonded nonwoven fabric layer formed the inner side and the meltblown nonwoven fabric layer formed the outer side. Then, the laminated nonwoven fabric was heated at 145° C. by the use of a heated air alternatively jetting type heater to obtain a nonwoven fabric of four-layer structure in which the spun bonded nonwoven fabrics were thermally fused to each other. The resultant laminated nonwoven fabric had a basis weight of 74 g/m², uniformity index of 0.28, vertical strength of 14.67 kg/5 cm, and lateral strength of 11.32 kg/5 cm. The apparent density of the meltblown nonwoven fabric was 0.052 g/cm³.

The laminated nonwoven fabric had a good texture and no fiber detachment. The fabric had no polymer particles and a delamination strength of 204 g/5 cm. The laminated nonwoven fabric was able to use for home-use wiping cloths as it was or after having being applied with one of a variety of lubricants by dipping or spraying method.

COMPARATIVE EXAMPLE 3

Polypropylene having a melting point of 165° C. and an MFR of 60 (230° C., g/10 minutes) was spun at a spinning temperature of 300° C. through spun bond spinning nozzles, for regular fiber, having an orifice diameter of 0.4 mm, the resultant fibers were aspirated by an air sucker at a velocity of 3000 m/minute and blown onto the net-conveyor together with air. The blown air was aspirated and removed by the use of an aspirating exhaustion apparatus installed under the net-conveyor. The resultant web was composed of regular fibers having a fineness of 1.5 d/f. The web was heated at 162° C. with a through-air type heater to obtain a nonwoven fabric in which the fibers were thermally fused in part. The nonwoven fabric had a basis weight of 18 g/m², uniformity index of 0.75, vertical strength of 2.10 kg/5 cm, and lateral strength of 1.35 kg/5 cm. The nonwoven fabric was heat-treated at a temperature slightly lower than the melting point of the fiber. However, the fabric had incomplete thermal fusion on one side thereof, and moreover, had wrinkles generated therein because of heat shrinkage occurred at the time of the heating.

A meltblown nonwoven fabric was prepared by the same preparation method as in Example 1. However, heat treatment by the air-through type heater after spinning was not carried out; spinning nozzles, for regular fibers, having an orifice diameter of 0.3 mm were used; polypropylene having a melting point of 166° C. and an MFR of 74 (230° C., g/10 minutes) was spun at a spinning temperature of 290° C., and heated air was blown under conditions of a heated air temperature of 380° C. and a pressure of 2.0 kg/cm² to obtain an extra-fine-fiber web. The resultant web had a fiber diameter of 3.2 μm. The web was a nonwoven fabric like product having thermally fused portions between fibers caused by the self-heating at the time of spinning. The nonwoven fabric had a basis weight of 18 g/m², uniformity index of 0.21, vertical strength of 0.72 kg/5 cm, lateral strength of 0.60 kg/5 cm, and apparent density of 0.078 g/cm³.

The spun bonded nonwoven fabric and the polypropylene meltblown nonwoven fabric both described above were laminated and heated at 162° C. by the use of the through-air-type heater as in Example 1 to obtain a laminated nonwoven fabric of two-layer structure having a basis weight of 39 g/m² in which the two layers were thermally fused in part. The laminated nonwoven fabric had a uniformity index of 0.63, vertical strength of 4.87 kg/5 cm, and lateral strength of 4.24 kg/5 cm. The nonwoven fabric was heat-treated at a temperature slightly lower than the melting point of polypropylene. However, the fabric had wrinkles therein because of heat-shrinkage. Apparent density of the meltblown nonwoven fabric determined after cutting the laminated fabric at laminated faces with a razor to separate them increased to 0.081 g/cm³ by the heat treatment after lamination.

The laminated nonwoven fabric had no fiber detachment, no polymer particles, and a delamination strength of 266 g/5 cm. The laminated nonwoven fabric had wrinkles therein and had a poor texture.

COMPARATIVE EXAMPLE 4

A meltblown nonwoven fabric was prepared by the same preparation method as in Example 1. However, spinning nozzles, for regular fiber, having an orifice diameter of 0.3 mm were used; heat treatment with a through-air type heater after spinning was not carried out; and polyethylene terephthalate having a melting point of 257° C. was spun at a spinning temperature of 300° C.; heated air was blown under conditions of a heated air temperature of 360° C. and a pressure of 1.8 kg/cm² to obtain an extra-fine-fiber web. The resultant web had an average fiber diameter of 5.2 μm. The web had little thermally fused portions between fibers caused by the self-heating at the time of spinning. When the web was pressed by hand and then the hand was moved off the web, the fibers detached from the web were present on whole surface of the hand. The web had a uniformity index of 0.22, basis weight of 16 g/m², vertical strength of 0.03 kg/5 cm, lateral strength of 0.01 kg/5 cm, and apparent parent density of 0.070 g/cm³.

The composite spun bonded nonwoven fabric obtained in Example 3 and the meltblown web described above were laminated and heated at 148° C. with a through-air type heater, as in Example 1, to obtain a laminated nonwoven fabric of two-layer structure in which the two layers were thermally fused in part. The nonwoven fabric had a basis weight of 39 g/m², uniformity index of 0.25, vertical strength of 4.63 kg/5 cm, and lateral strength of 3.92 kg/5 cm. Apparent density of the meltblown nonwoven fabric determined after cutting the nonwoven fabric with a razor at laminated surfaces to separate them was 0.072 g/cm³. The delamination strength was 4.9 g/5 cm.

The laminated nonwoven fabric had a good texture and no polymer particles. However, many fibers were detached from the web, and thus it was judged to be bad in fiber detachment resistance.

EXAMPLE 5

The composite spun bonded nonwoven fabric obtained in Example 1 and the sheath-core type composite meltblown extra-fine-fiber nonwoven fabric obtained in Example 2 were laminated and pressed with heated emboss rolls. As the rolls, a combination of a calendering roll and an emboss roll in which the area of the convex portion is 15% of the whole area was used, and the meltblown nonwoven fabric was arranged to contact with the emboss roll. Conditions for pressing under heating were such that the temperature of the embossing rolls was 120° C., the temperature of the calender rolls was 120° C., and the linear pressure was 25 kg/cm.

The laminated nonwoven fabric had a uniformity index of 0.26 and a basis weight of 35 g/m². Apparent density of the composite meltblown extra-fine-fiber nonwoven fabric determined after cutting the nonwoven fabric with a razor at laminated surfaces to separate them was 0.11 g/cm³. The laminated nonwoven fabric had a vertical strength of 8.92 kg/5 cm, lateral strength of 7.65 kg/5 cm, and delamination strength of 827 g/5 cm.

The laminated nonwoven fabric had a good texture, no polymer particles, and no fiber detachment.

EXAMPLE 6

A composite meltblown extra-fine-fiber nonwoven fabric was prepared by the same preparation method as in Example 1. However, a high density polyethylene having a melting point of 135° C. and an MFR of 28 (190° C., g/10 minutes) was used as the first component and spun at a spinning temperature of 280° C.; polypropylene having a melting point of 166° C. and an MFR of 36 (230° C., g/10 minutes) was used as the second component and spun at a spinning temperature of 260° C.; heated air was blown under conditions of a heated air temperature of 340° C. and a pressure of 2.1 kg/cm², and a side-by-side extra-fine composite fiber nonwoven fabric having a composite ratio of 50/50 (% by weight) was obtained. The resultant web had a fiber diameter of 7.6 μm. The web was a nonwoven fabric like product having thermally fused portions between fibers caused by the self-heating at the time of spinning. Then, the nonwoven fabric was heated at 145° C. by using an air-through type heater to obtain a nonwoven fabric having thermally fused portions. The resultant nonwoven fabric had a basis weight of 20 g/m² and was found to have few polymer particles by tactile inspection. The nonwoven fabric had a uniformity index of 0.32, vertical strength of 1.77 kg/5 cm, lateral strength of 1.09 kg/5 cm, and apparent density of 0.046 g/cm³.

The composite spun bonded nonwoven fabric obtained in Example 1 and the composite meltblown nonwoven fabric described above were laminated and heated at 145° C. as in Example 1 to obtain a laminated nonwoven fabric of two-layer structure in which the two layers were thermally fused in part. The laminated nonwoven fabric slightly increased in basis weight to 39 g/m² by the heat treatment of the laminated product. The laminated nonwoven fabric had a uniformity index of 0.26, vertical strength of 5.03 kg/5 cm, and lateral strength of 4.16 kg/5 cm. Apparent density of the meltblown nonwoven fabric determined after cutting the laminated nonwoven fabric with a razor at laminated surfaces to separate them was slightly increased to 0.051 g/cm³ by the heat treatment after lamination. The laminated nonwoven fabric had a delamination strength of 203 g/5 cm.

The laminated nonwoven fabric had no fiber detachment. The meltblown nonwoven fabric had 2.8 polymer particles per square meter. The laminated nonwoven fabric had a good flexibility, had a little rough feeling due to the particles. The laminated nonwoven fabric can be used for thermal-insulation material and filtering material.

EXAMPLE 7

Using a commercial disposable diaper which had a shape of roughly I (cross-sectional shape of rail) when unfolded flat, only the top material of the disposable diaper in the vicinity of the portions which abut on the user's legs were replaced by the laminated nonwoven fabric obtained in Example 1.

The disposable diaper is composed of polyethylene/polypropylene thermally fusible composite fiber staples; and includes (a) a nonwoven fabric in which fibers are thermally fused at their junctions as the top material, (b) a water absorbing material including pulp and highly absorbent resin as the main component, and (c) a polyethylene film as the bottom material. Only the nonwoven fabric of the diaper in the vicinity of both of the leg-abutting portions were removed by the use of a knife. The laminated nonwoven fabric obtained in Example 1 was laminated on the portions in the vicinity of both of the leg-abutting portions such that the composite meltblown extra-fine-fiber nonwoven fabric layer faced the skin and the composite spun bonded nonwoven fabric layer faced the polyethylene film as the bottom material. Three polyurethane elastomer threads were disposed between the top material and the bottom material in a stretched condition. The portions in the vicinity of the center portion of remaining nonwoven fabric and the laminated nonwoven fabric were thermally fused, and then the bottom material described above and the laminated nonwoven fabric were thermally fused. The remaining portion of the laminated nonwoven fabric was removed by the use of scissors to obtain a disposable diaper in which the composite melt-blown extra-fine-fiber nonwoven fabric was arranged to face to the skin of the user's legs. The diaper assumed the shape of an arch due to the elastomer threads placed on the leg-abutting portions. The diaper had a soft texture at the leg-abutting portions and was able to prevent liquid from leaking from the same because of the water-repellency of the meltblown nonwoven fabric. The disposable diaper was especially suitable for newborn babies.

INDUSTRIAL APPLICABILITY

The laminated nonwoven fabric of the present invention comprises a composite spun bonded nonwoven fabric laminated on a composite meltblown extra-fine-fiber nonwoven fabric. The laminated nonwoven fabric exhibits an excellent texture and has an improved strength of nonwoven fabric. Moreover, since fibers are thermally fused to one another at the junctions thereof in the composite meltblown extra-fine-fiber nonwoven fabric, and the fabric is also thermally fused to the low-melting point component or the like of a composite spun bonded nonwoven fabric of continuous fiber, the delamination strength is increased and detachment of fiber is prevented. Further, since no polymer particles are produced, the laminated nonwoven fabric of the present invention provides neither rough texture nor irritation of skin.

What is claimed is:

1. A laminated nonwoven fabric of multi-layer structure comprising a composite spun bonded nonwoven fabric laminated on a composite meltblown extra-fine-fiber nonwoven fabric having an average fiber diameter of 10 μm or less; wherein the composite spun bonded nonwoven fabric comprises a composite continuous fiber composed of a low melting point resin and a high melting point resin, the difference in melting point between the low melting point resin and the high melting point resin being at least 10° C., the low melting point resin forming at least a portion of the surface of the fiber, and the composite spun bonded nonwoven fabric being a thermal fusion product of the composite continuous fibers by the mediation of the low melting point resin, the composite meltblown extra-fine-fiber nonwoven fabric comprises composite meltblown extra-fine fibers composed of a low melting point resin and a high melting point resin, the difference in melting point between the low melting point resin and the high melting point resin being at least 10° C., the low melting point resin forming at least a portion of the surface of the fiber, and the composite meltblown extra-fine-fiber nonwoven fabric being a thermal fusion product of the extra-fine fibers by the mediation of the low melting point resin; and the composite spun bonded nonwoven fabric and the composite melt-blown extra-fine-fiber nonwoven fabric are integrated by fusion of the low melting point resin of the composite spun bonded nonwoven fabric and/or the low melting point resin of the composite meltblown extra-fine-fiber nonwoven fabric.

2. A laminated nonwoven fabric according to claim 1, wherein the composite spun bonded nonwoven fabric comprises composite continuous fibers having a fineness of 0.5–10 d/f, the composite meltblown extra-fine-fiber nonwoven fabric comprises extra-fine fibers having a fiber diameter of 0.1–10 μm, has 10/m$^2$ or less of polymer particles having a diameter of at least 0.1 mm, and has an apparent density of 0.02–0.20 g/cm$^3$; and the laminated nonwoven fabric has a strength in the lateral direction of 0.6 kg/5 cm or more, uniformity index of 0.6 or less, and a delamination strength between the two layers of 6 g/5 cm or more.

3. An absorptive product comprising a laminated nonwoven fabric defined in claim 1 as at least one component of the product.

4. An absorptive product according to claim 3, wherein the product comprises a nonwoven fabric of double-layer structure composed of a composite spun bonded nonwoven fabric and a composite meltblown extra-fine-fiber nonwoven fabric; or a nonwoven fabric of multi-layer structure comprising at least three layers, composed of a composite spun bonded nonwoven fabric and a composite meltblown extra-fine-fiber nonwoven fabric, and having the composite melt-blown extra-fine-fiber nonwoven fabric laminated on at least one side of the laminated nonwoven fabric.

5. A method of manufacturing a laminated nonwoven fabric comprising the steps of:

spinning composite continuous fibers from a low-melting point resin and a high melting point resin so that at least a portion of the fiber surface is formed by the low-melting point resin, the difference in melting point between the low melting point resin and the high melting point resin being at least 10° C., and forming a spun bonded web by a composite spun bonding method; or heating the resultant fiber web at a temperature not lower than a thermal fusion temperature thereby to form a nonwoven fabric in which the fibers are thermally fused;

spinning composite meltblown extra-fine-fibers having an average fiber diameter of 10 μm or less, and comprising a low-melting point resin and a high melting point resin, the difference in melting point between the low melting point resin and the high melting point resin is at least 10° C., in such a fashion that the low-melting point resin forms at least a portion of the fiber surface, and forming a composite extra-fine-fiber web which does not include thermally fused portions by self-heating at the time of spinning, or forming a nonwoven fabric which includes portions thermally fused by self-heating at the time of spinning by a composite melt-blowing method; or forming a composite extra-fine-fiber nonwoven fabric in which the fibers are thermally fused by heating the spun fiber web or the nonwoven fabric which includes thermally self-fused portions at a temperature not lower than a thermal fusion temperature;

laminating the spun bonded web or the thermally fused nonwoven fabric, and the composite melt-blown extra-fine-fiber web or a composite melt-blown extra-fine-fiber thermally-fused nonwoven fabric; and heating the resultant laminate at a temperature not lower than the temperature at which the two layers become thermally fused.

6. A method of manufacturing a laminated nonwoven fabric according to claim 5, wherein the method further comprises a step of causing entanglement of the fibers in the webs or nonwoven fabrics of the two layers by a needle-punch or spun lace means before or after heating.

7. A method of manufacturing a laminated nonwoven fabric according to claim 6, wherein the laminate is heated with a through-air type heater at least at a thermal fusion temperature of the two layers.

8. A method of manufacturing a laminated nonwoven fabric according to claim 5, wherein the two layers are press-bonded under heating by the use of emboss rolls having a thermal press-bonding area of 5–25%.

9. A method of manufacturing a laminated nonwoven fabric according to claim 5, wherein the composite spun-bonded nonwoven fabric and the composite melt-blown extra-fine-fiber nonwoven fabric each having a uniformity index of 0.6 or less are used as nonwoven fabric.

10. A method of manufacturing a laminated nonwoven fabric according to claim 5, wherein the two layers are heated with an alternatively hot-air jetting heater such that hot air is jetted from the top face side and the bottom face side of the nonwoven fabric of multi-layer structure in an alternating manner.

11. An absorptive product comprising a laminated nonwoven fabric defined in claim 2 as at least one component of the product.

12. A method of manufacturing a laminated nonwoven fabric according to claim 6, wherein the two layers are press-bonded under heating by the use of emboss rolls having a thermal press-bonding area of 5–25%.

13. A method of manufacturing a laminated nonwoven fabric according to claim 6, wherein the composite spun-bonded nonwoven fabric and the composite melt-blown extra-fine-fiber nonwoven fabric each having a uniformity index of 0.6 or less are used as nonwoven fabric.

14. A method of manufacturing a laminated nonwoven fabric according to claim 6, wherein the two layers are heated with an alternatively hot-air jetting heater such that hot air is jetted from the top face side and the bottom face side of the nonwoven fabric of multi-layer structure in an alternating manner.

* * * * *